United States Patent
Roland et al.

(10) Patent No.: US 10,551,456 B2
(45) Date of Patent: Feb. 4, 2020

(54) METHOD AND APPARATUS FOR GENERATION OF IMAGE DATA BASED ON MR THERMOMETRY DATA

(71) Applicants: Joerg Roland, Hemhofen (DE); Eva Rothgang, Nuremberg (DE); Michael Suehling, Erlangen (DE)

(72) Inventors: Joerg Roland, Hemhofen (DE); Eva Rothgang, Nuremberg (DE); Michael Suehling, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1114 days.

(21) Appl. No.: 14/179,860

(22) Filed: Feb. 13, 2014

(65) Prior Publication Data

US 2014/0243654 A1     Aug. 28, 2014

(30) Foreign Application Priority Data

Feb. 28, 2013  (DE) .......................... 10 2013 203 407

(51) Int. Cl.
| | |
|---|---|
| G01R 33/48 | (2006.01) |
| G06T 11/00 | (2006.01) |
| A61B 5/00 | (2006.01) |
| A61B 90/00 | (2016.01) |
| A61B 5/055 | (2006.01) |
| A61B 17/00 | (2006.01) |
| G01R 33/56 | (2006.01) |
| G01R 33/54 | (2006.01) |

(52) U.S. Cl.
CPC ........ *G01R 33/4804* (2013.01); *G06T 11/003* (2013.01); *A61B 5/055* (2013.01); *A61B 5/743* (2013.01); *A61B 5/7425* (2013.01); *A61B 2017/00084* (2013.01); *A61B 2090/374* (2016.02); *G01R 33/543* (2013.01); *G01R 33/5608* (2013.01)

(58) Field of Classification Search
CPC .... A61B 2017/00084; A61B 2090/374; A61B 5/055; A61B 5/7425; A61B 5/743
See application file for complete search history.

(56) References Cited

U.S. PATENT DOCUMENTS

| | | | | |
|---|---|---|---|---|
| 5,327,884 | A | * | 7/1994 | Hardy .................... A61B 18/24 600/411 |
| 5,514,962 | A | * | 5/1996 | Cline .................... G01R 33/54 324/307 |

(Continued)

OTHER PUBLICATIONS

Joblove et al., "Color Spaces for Computer Graphics," pp. 20-25, Program of Computer Graphics, Cornell University, ACM Siggraph Computer Graphics; (1978).

(Continued)

*Primary Examiner* — Amelie R Gillman
(74) *Attorney, Agent, or Firm* — Schiff Hardin LLP (57) ABSTRACT

In a method, apparatus and medical imaging system to generate image data based on magnetic resonance (MR) thermometry data, planning data of a region of an examination subject that is to be depicted thermometrically are provided to a processor. Through the processor, segmentation data based on the planning data are generated MR thermometry data are provided to the processor, which generates image data on the basis of the MR thermometry data, using the segmentation data.

7 Claims, 4 Drawing Sheets

(56) References Cited

U.S. PATENT DOCUMENTS

| | | | |
|---|---|---|---|
| 5,916,161 A * | 6/1999 | Ishihara | A61B 5/055 324/315 |
| 2006/0184163 A1* | 8/2006 | Breen | A61B 18/04 606/20 |
| 2008/0061779 A1 | 3/2008 | Feiweier | |
| 2009/0220050 A1* | 9/2009 | Guhring | A61B 5/055 378/98.5 |
| 2010/0312094 A1* | 12/2010 | Guttman | A61B 5/415 600/411 |
| 2011/0178386 A1* | 7/2011 | Grissom | G01R 33/4804 600/410 |
| 2011/0241668 A1* | 10/2011 | Beckmann | A61B 5/015 324/307 |
| 2012/0070058 A1 | 3/2012 | Raju et al. | |
| 2012/0133362 A1 | 5/2012 | Gross | |
| 2012/0172708 A1 | 7/2012 | Anand et al. | |
| 2013/0131433 A1 | 5/2013 | Katscher et al. | |

OTHER PUBLICATIONS

Senneville et al.; "Magnetic resonance temperature imaging"; Taylor &Francis Group, Int. J. Hyperthermia, Magnetic resonance temperature imaging; vol. 21; No. 6; pp. 516-531; ISSN: 0265-6736; (2005).

R. Salomir et al. "Reference-Free PRFS MR-Thermometry Using Near Harmonic 2D Reconstruction of the Background Phase"—IEEE Transactions on Medical Imaging, vol. 31, pp. 287-301 ( 2012).

Zheng et al., "Research Progress on Temperature Measurement Technique During High Intensity Focused Ultrasound Treatment," Chinese Journal of Bone Tumor and Bone Disease, vol. 9, No. 1, pp. 84-87 (2010).

\* cited by examiner

METHOD AND APPARATUS FOR GENERATION OF IMAGE DATA BASED ON MR THERMOMETRY DATA

BACKGROUND OF THE INVENTION

Field of the Invention

The present invention concerns a method to generate image data based on magnetic resonance thermometry data; an image data generation unit to generate image data on the basis of magnetic resonance thermometry data; a medical imaging system with such an image data generation unit; and a medical imaging system with an ablation system.

Description of the Prior Art

"Thermometry" designates the science of temperature measurement or generally methodology for determining temperatures, and in particular spatial and/or temporal temperature distributions. In medicine, thermometry is used in numerous ways. Some of these medical applications require thermometric detection and the depiction of regions of the inside of a patient (examination subject).

One known method for thermometric detection of regions of the interior of a patient is the generation of magnetic resonance thermometry data (abbreviated in the following as MR thermometry data). The thermally dependent change of magnetic resonance measurement values is determined with a magnetic resonance system. For example, the longitudinal relaxation time of hydrogen protons, the molecular diffusion coefficient of hydrogen protons, and the shift of the magnetic resonance frequency of hydrogen protons, are suitable magnetic resonance measurement values for this purpose. Various methods to generate MR thermometry data are described in the article "Magnetic resonance temperature imaging" (Int. J. Hyperthermia, September 2005; 21(6): 515-531) by B. Denis de Senneville, for example.

In the generation of "real-time thermometry image data" or "live thermometry image data" from measured thermometry data, the measurement and depiction of MR thermometry data takes place from which thermometry image data can be reconstructed for further presentation, preferably with a relatively low spatial resolution. The low spatial resolution enables an accelerated measurement, calculation and generation of a presentation of the MR thermometry data, and thus a relatively high "temporal resolution". For example, a "real-time reconstruction" or "live reconstruction" of MR thermometry data can take place with sufficient spatial resolution when the underlying measurements take place at a frequency of more than two images per second (preferably more than five images per second), with the raw magnetic resonance data on which the respective images are based being acquired at different time periods.

Although the low spatial resolution of the live thermometry image data is well-suited for thermometry, practical usage of the live images in the everyday clinical environment is difficult. Many applications require additional information that can be identified only with difficulty—or that is not included at all—in the live images.

SUMMARY OF THE INVENTION

An object of the present invention is to avoid this disadvantage, and to improve the usability of MR thermometry data.

The method according to the invention for generation of image data includes the following steps:

In an initial step, planning data of a region of an examination subject that is to be depicted or imaged thermometrically are acquired and provided to a processor. The planning data can be an image data set that can be used for planning and implementation of a thermal ablation. Preferably this is a high resolution data set. In particular, the data can be a 3D volume data set or a slice stack of 2D slice images (2D slice stack). For example, the planning data can be computed tomography data, ultrasound data, or (preferably) magnetic resonance tomography data. The planning data are preferably in a format corresponding to the DICOM (Digital Imaging and Communications in Medicine) standard, which enables image data to be used and exchanged independently of the modality for generation of the image data. DICOM standardizes both the format to store the data and the communication protocol for exchange of the data.

In a further step of the method according to the invention, segmentation data are generated. The segmentation data are based on the planning data. Spatial boundaries of segmented structures can thereby be identified, and information is obtained about the ability to associate a defined pixel or voxel of the planning data with a segmented structure in the segmentation data. Segmented structures in particular describe one or more spatially contiguous regions. These are thereby typically organs, bones, blood vessels or other structures (for example lesions, tumors, already-ablated structures, contrast agent-enriched structures or implants) that are presented in the segmentation data. In the segmentation of organs, a differentiation is preferably made between organs that are to be treated thermally, organs that are not to be damaged, and other organs. This classification of the structures, as well as the designation ("tag") of the respective structure, can be included in the segmentation data. The segmentation data can relate to a number of segmented structures, meaning that one or more segmented structures can be described by the segmentation data.

For example, if the planning data are present in the DICOM standard, the planning data can also include supplementary information, for example. For example, this supplementary information can include segmentation information from segmentation steps that have already taken place; surface definitions; and possible information about image registrations that have already taken place. For example, the generation of the segmentation data can then take place at least in part by the adoption of supplementary information of the planning data into the segmentation data.

In a further step of the method according to the invention, magnetic resonance thermometry data (MR thermometry data) are acquired. The MR thermometry data are preferably based on the aforementioned magnetic resonance measurement variables. The MR thermometry data are raw thermometry data, for example, raw magnetic resonance data from which a magnetic resonance image can be calculated. The MR thermometry data preferably include a magnitude image and/or a phase image of a region of the examination subject that is to be depicted thermometrically. The raw thermometry data are also be added to the magnitude and phase images since temperature information that is intuitively understandable for a user (for example in the form of color or greyscale values of individual pixels or voxels) is typically not shown in these images. Further analysis of the MR thermometry data is necessary to calculate a presentation of such intuitively understandable temperature information, such that "MR thermometry image data" generated from the MR thermometry data ultimately include the desired intuitive temperature information.

The thermometry data are preferably data that are suitable for reconstruction of the aforementioned real-time or live thermometry image data. This means that the magnetic resonance data acquisition to generate the thermometry data takes place so quickly that a reconstruction of thermometry image data is possible with a frequency (i.e. a frame rate) that is preferably more than two images per second and more preferably five images per second or more.

The term "high-resolution" that is used above with regard to the planning data in the preceding is defined in relation to the MR thermometry data, and means that the planning data are preferably of higher resolution than the MR thermometry data. It is also conceivable for the planning data to have a higher contrast or a different type of contrast than the MR thermometry data. A higher contrast means that the value range of color or greyscale values that are used for presentation is larger or is more finely graded. A different type of contrast means that a fundamentally different type of excitation sequence is used to generate the planning data than is used to generate the MR thermometry data. For example, the planning data can be generated with the use of a GRE sequence (gradient echo sequence) and the thermometry data can be based on a TSE sequence (turbo spin echo sequence). Moreover, EPI (=echoplanar imaging) or other sequences can be considered as additional types of excitation sequences.

An additional step of the method according to the invention concerns the generation of image data based on MR thermometry data using the segmentation data.

The image data preferably include the desired intuitive temperature information, meaning that the generated image data can be the MR thermometry data generated according to the invention. By consideration of the segmentation data, it is possible to improve the presentation of the MR thermometry data so that information included therein is presented in a manner so as to be intuitively usable by a user. The use of the MR thermometry data is thus improved for a number of applications. As is explained in more detail in the following, the information included therein can be limited to an organ, for example; noise/artifacts in other structures can be masked out automatically. As explained below, the use of segmentation data in the generation of MR thermometry image data also enables an improvement of the thermometry. This improvement is that the temperature information included or coded in the MR thermometry data can be calculated more precisely relative to conventional methods.

The invention also encompasses an image data generation unit, which is designed to generate image data based on MR thermometry data. According to the invention, the image data generation unit includes a planning data interface that receives the planning data (in particular the high-resolution 3D planning data), as well as a segmentation module to determine segmentation data on the basis of the planning data. For example, the segmentation module can also be an interface if the planning data have already been segmented (for example as indicated with regard to planning data in the form of DICOM data), such that the segmentation module can use already-present segmentation data or segmentation information. However, the segmentation module is normally designed (using a calculation unit that segments the data according to a typical method such as edge detection, region growing or a model-based method, for example) to isolate or show in isolation specific structures to be segmented.

The image data generation unit also has a thermometry data interface to receive MR thermometry data. In particular, the interface is designed to accept MR thermometry data in the form of magnitude images and/or phase images. The thermometry data interface can also include a reconstruction unit that can reconstruct the mentioned phase image and/or the magnitude image from raw magnetic resonance data.

Furthermore, the image generation unit according to the invention has an image data calculation module that generates image data based on the MR thermometry data using the planning data. This means that the image data calculation module is designed to calculate data for a graphical presentation of the MR thermometry data that also take into account information from the planning data. In particular, the information considered is the segmentation data. It is thus not required that this involve a presentation of the thermometry image data. However, it is advantageous that the MR thermometry data are used to generate the image data. For example, position information can be determined based on the thermometry data and used to generate the image data.

The image data generated according to the invention can be visualized at a suitable display unit.

Furthermore, the invention encompasses a medical imaging system that has an image data generation unit according to the invention. It is likewise possible for the imaging system to include the display unit.

The invention also concerns a medical imaging system with an ablation system that is controllable using the image data generated with a method of the invention. "Using the image data" means that the image data are made available to the user of the ablation system during an ablation procedure so that the user can use the image data to control the ablation. This means that the image data are preferably displayed to the user of the ablation system during the ablation procedure, for example via a display unit of the ablation system. For this purpose, the medical imaging system and/or the ablation system can include the image data generation unit according to the invention.

It is also possible for the image data generated with a method of the invention to be used for semi-automatic or fully automatic control of the ablation system. In this case, the display of the image data generated according to the invention could also be omitted during the ablation. For example, the image data generated according to the invention can then wholly or at least partially replace the planning data, preferably in a semi-automatic or automatic implementation of the ablation.

A wholly automatic real-time feedback during the ablation is thus possible, meaning that the planning data set used to control an ablation system has image data generated according to the invention that enable or, respectively, produce a variation of the control of the ablation relative to the original plan. For this purpose, the ablation system has a suitably designed control interface in order to be able to use the image data as control data to control the ablation.

Significant portions of the image data generation unit are preferably realized in the form of software running in a suitable programmable computer, for example of the medical imaging system and/or ablation system, with appropriate storage capabilities. This particularly concerns the segmentation module and the image data calculation module. The planning data interface and the thermometry data interface (which can also be fashioned as a single, common interface) can be, for example, interfaces that select and accept data from a data store arranged within the medical imaging system and/or ablation system (or connected with this via a network), possibly also using a user interface. Furthermore, the systems can respectively have output interfaces in order to pass the generated data to other devices for further processing, presentation, storage, etc. A realization largely in software—particularly of the segmentation module and the image data calculation module—has the advantage that image data generation units or the like that have already previously been in use can be retrofitted simply via a software update in order to operate in the manner according to the invention.

Therefore, the above object also is achieved by a non-transitory data storage medium, which may be portable, which is encoded with programming instructions that can be loaded directly into one or multiple memories of the medical imaging system and/or of the ablation system. The programming instructions include program code segments in order to execute all steps of the method according to the invention when the program is executed in the image data generation unit. The storage medium can be a non-volatile memory, such that the programming instructions can be reproducibly loaded from this memory into the image data generation unit.

In an embodiment of the method according to the invention, MR thermometry data and at least a portion of the planning data are brought into registration with one another. For example, the spatial position of the phase image or magnitude image in the 3D data set is determined. For example, DICOM information that is included in the planning data and/or the thermometry data can also be used for this. Movement correction information of the magnetic resonance imaging system can also be used in order to improve the registration of the thermometry data and the planning data. For example, movement correction information can exist on the basis of a non-rigid (elastic) registration, be generated with the use of MR navigators and be present in the form of translation vectors (for example). The use of MR navigators (i.e. navigator signals or "navigator echoes") for movement correction is described in the published German Patent Application DE 10 2006 042 998 A1, for example. In the same manner, the MR thermometry image data (that are generated from the MR thermometry data) and at least a portion of the planning data could also be registered with one another.

It is thus possible to use the planning data and the thermometry data for a joint presentation. The information that can be presented to a user thus can be significantly extended. In particular, this can significantly increase the usable value range of color or greyscale values of adjacent pixels or voxels, such that an improved contrast (i.e. the maximum difference of color or greyscale values) of the image data is achieved. The resolution of the thermometry image data can also be improved. For example, the generated image data can have a higher resolution relative to the thermometry data (which, for example, can be reconstructed or can be present as a magnitude and/or phase image). The resolution of the generated image data is preferably identical to the resolution of the planning data.

As was mentioned above, the planning data can be acquired with a different type of excitation data than the thermometry data. The respective data ("planning data" or "thermometry image") thus have a different type of contrast. For example, the different type of contrast can be generated by the acquisition of different resonance times, for example the T1 or T2 resonance times. At least one different resonance time (for example T1) is preferably used to generate the planning data than is used to generate the thermometry data (T2, for example).

A modification of the method according to the invention improves the presentation of the thermometry data to the effect that the MR thermometry data used to generate the image data are limited depending on structures segmented from the planning data. This means that the MR thermometry data used to generate the image data are limited depending on structures segmented from the planning data. This means that MR thermometry data which describe the region enclosed by the segmented structures can be selected and used to generate image data. The thermometry data that describe the region outside of the enclosed region are then not used to generate image data. The segmented structures thus essentially form a mask for selection of the thermometry data that are selected for graphical presentation. The presentation of the image data for the user of an ablation system can thus be limited directly to the information that concerns a region of interest (ROI) to him or, respectively, the ablation. For example, a tumor and an adjoining blood vessel that is not to be injured can be selected as a segmented structure. The image data generated via the corresponding [sic] the described modification then reflect MR thermometry data only for regions that lie within the selected segmented structures.

The segmented structures can furthermore also be used in order to determine background phase data to create a proton resonance frequency shift thermometry image, abbreviated as a "PRFS image". For example, the creation of PRFS images is described in the article by R. Salomir et al., "Reference-Free PRFS MR-thermometry using near harmonic 2D reconstruction of the background phase", "IEEE Transactions On Medical Imaging", Vol. 31, 2, 2012, P. 287 to P. 301.

In particular, it is known to generate what are known as "referenceless" or "referencefree" PRFS MR thermometry image data. "Referenceless" or "referencefree" in this context means that a region is selected from a phase image, which region is used to reconstruct background phase data that essentially serve as a reference for a temperature increase or, respectively, decrease that is to be determined. In contrast to this, PRFS MR thermometry data that are generated with the use of a reference (and thus are not "referenceless" data) are based on phase data that are determined from MR thermometry data of the same spatial region that are acquired at different points in time.

The invention for the first time allows the region used for reconstruction of the background phase from the phase image to be selected with the use of segmentation data that are taken from a planning data set. In particular, a fully automatic selection for the region that is used to calculate the background phase can thus take place. This is especially advantageous for thermal ablation methods since in such methods the elevation of the temperature relative to an adjoining region (that is not to be injured, for example) is particularly important. The segmentation can simultaneously have been relatively coarse, meaning that the organ or, respectively, tumor boundaries do not need to be followed exactly in order to nevertheless achieve a significant improvement of the PRFS MR thermometry images. The improvement thereby in particular relates to a more exact temperature determination relative to known referenceless or referencefree PRFS images that are based on the region that determines the background phase being predetermined by hand.

The generated image data then preferably include a PRFS thermometry image.

In one development of the invention, the image data have a representation and/or an identification of the segmented structure. The spatial support or position of the region of the examination subject that is acquired with the use of the MR thermometry data is preferably identified in the depiction of a segmented structure, based on the segmentation data. The image data thus directly reflect the information with regard to the region of a segmented structure (an organ, for example) for which the MR thermometry data have been acquired.

The depiction of the segmented structure preferably includes a spatial presentation of the segmented structure, meaning that the segmented structure is at least shown in perspective, in relation to anatomical references. The presentation of the segmented structure can preferably be shown so as to be rotatable around a rotation axis. For example, the rotation can be implemented via a user interface of the image data generation unit.

For example, the spatial presentation—in connection with the described identification of the spatial position of the region acquired with the aid of the MR thermometry data—can then be used in order to replace what is known as an "orientation cube" in the generated image data with a more intuitive presentation. However, it is not precluded for an "orientation curve" to still be additionally incorporated into the image data, for example in order to identify the bearing of the region that is acquired via the MR thermometry data relative to a patient bed of the magnetic resonance imaging system.

Furthermore, a 3D model of the region, or of a segmented region that is to be depicted thermometrically, can be created with the use of the segmentation data. As mentioned above the segmentation data can include a "tag" that identifies and/or classifies the segmented structure. With the use of the tag it is possible to select a matching model in a database to represent the segmented structure. For example, the image data then include a depiction of the 3D model selected from the database. The spatial position of the region of the examination subject that is acquired with the use of the MR thermometry data is preferably identified in the presentation of the 3D model. The "creation of a 3D model" in this context means that at least one standard model of a segmented structure is adapted to the real, relative spatial intervals of points of the examination subject. The generated 3D model then reflects the spatial intervals of points of the segmented structure relative to one another according to the real relationships of the examination subject.

For example, the possibility is provided to particularly quickly calculate image data, that facilitates an intuitive orientation with regard to the segmented structure in an examination subject, by the use of a 3D model, and preferably (for example) of an advantageously continuous identification of the thermometry data in the 3D model. In this case, for example, the generated image data can be used for precise control of a thermal ablation.

In the same manner as explained above, it is also possible to use this presentation variant instead of an "orientation cube".

The image data preferably include a fusion (i.e. a superposition) of an MR thermometry image or of MR thermometry image data (that are generated with the use of the MR thermometry data) with a presentation of the planning data or with planning data. With the use of this superposition (which is preferably calculated as a weighted superposition) it is possible to markedly improve the contrast of the generated image data relative to the original MR thermometry image data (which are based purely on MR thermometry data). This means that the value range that is used for coding of temperature and structure information in the form of color or greyscale values is markedly larger and/or more finely graded than would be possible for the thermometry image data, which are based exclusively on live they data. Moreover, it is possible to combine fundamentally different types of contrast, for example T1 or T2 contrasts. For example, the T1 contrasts can be taken from the planning data and the T2 contrasts can be taken from the thermometry data. This can also advantageously be used for an ablation, for example in that regions that are critical to the ablation (blood vessels, for example) are more clearly emphasized in the generated image data.

Moreover, the generated image data can also similarly include a fusion of an MR thermometry image (generated with the aid of the MR thermometry data) with a representation of a 3D model of the region of the examination subject that is to be depicted thermometrically or, respectively, a representation of a 3D model of a segmented structure.

The advantages of a fast calculation of the MR thermometry image data are thus combined with the advantage of a fast calculation of the presentation of a 3D model, for example such that frame rate of five images per second is easily possible.

DESCRIPTION OF THE PREFERRED EMBODIMENTS

Figure 1:
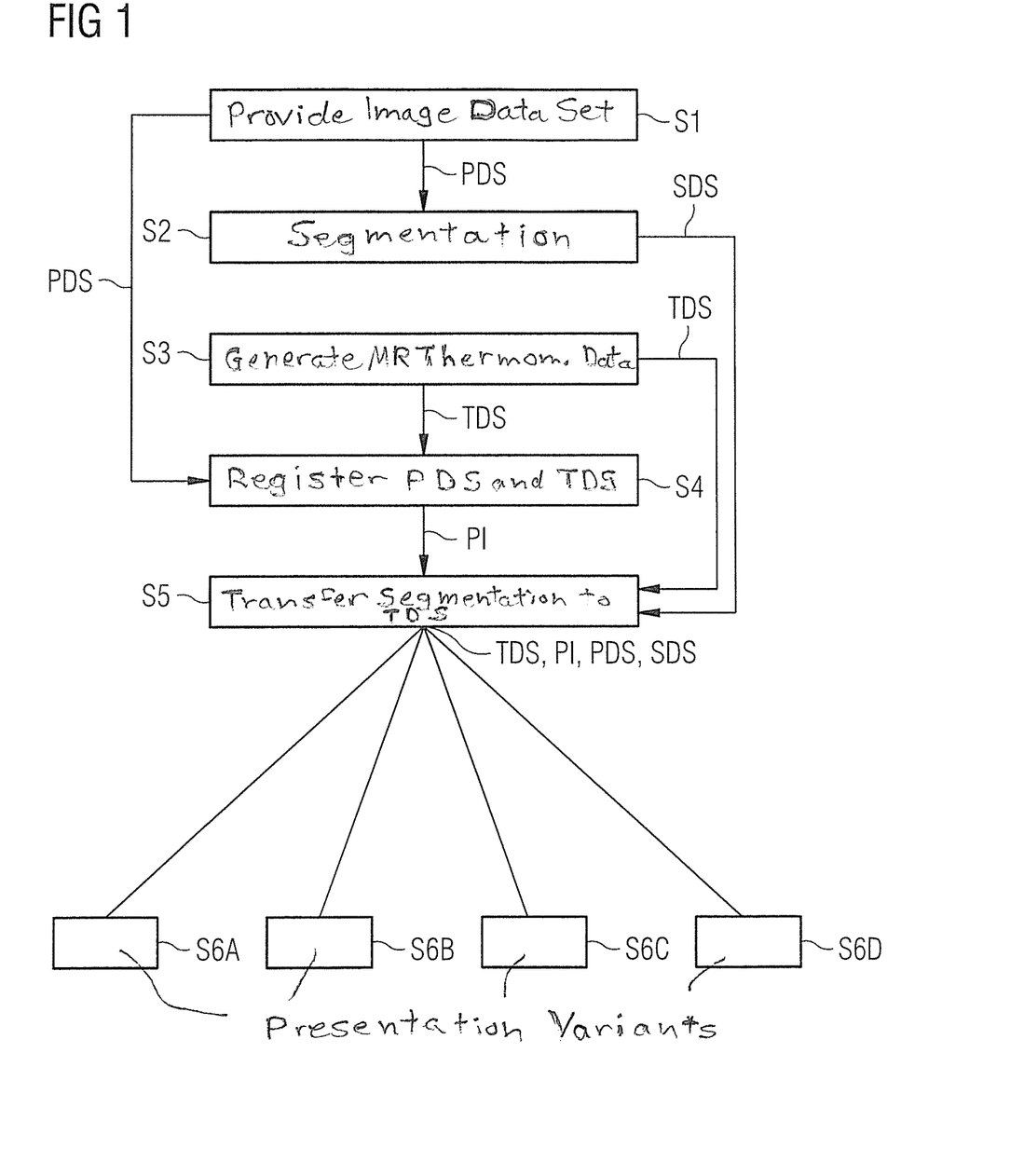
FIG. 1 shows multiple embodiments of the method according to the invention for generation of image data in a flowchart.

In a flowchart, FIG. 1 shows multiple variants of a method according to the invention for generation of image data. These variants can be used individually or in combination.

In an initial Step S1 of the method according to the invention, a high-resolution 3D data set is provided. In the exemplary embodiment it is a planning data set PDS for a thermal ablation. The planning data set PDS thereby exists as a stack of two-dimensional slice images of a region of an examination subject in which the thermal ablation should be implemented. The slices images are thereby present in DICOM-coded form, wherein the position of the slice images relative to one another is described. For example, this DICOM information can be used in order to control a subsequent thermal ablation.

In a subsequent Step S2, the segmentation of one or more segmented structures or, respectively, the establishment of one or more "Region(s) of Interest" for the subsequent thermal ablation takes place on the basis of the planning data PDS. Segmentation data SDS are thereby generated as mentioned in the preceding. In particular, the segmentation can take place automatically and a user can select one or more "Region(s) of Interest" for the subsequent ablation, for example using the mentioned "tags". For example, the possibility of subsequent, additional, manual modifications of the segmentation data (for example a variation of the shape of segmented structures) can also be provided.

In a further Step S3 of the method, magnetic resonance data are acquired and a magnitude image and phase image are, reconstructed which can be used as MR thermometry data TDS to generate PRFS magnetic resonance thermometry image data.

The order of the implementation of Steps S1 and S3 is thereby insignificant and can be varied arbitrarily. In particular, it is conceivable to execute multiple Steps S1 through S3 simultaneously.

According to Step S4, the registration of the MR thermometry data TDS with the planning data PDS takes place. In the event of a repetition of the method according to the invention, this registration does not need to be implemented for all newly generated MR thermometry data TDS. After an initial registration, for example, a DICOM information of the thermometry data TDS can preferably be used in connection with a motion correction information in order to achieve a registration of equivalent data. After the registration, position data PI exist that describe which pixels of the MR thermometry data TDS—and therefore also of the MR thermometry image data—are associated with defined pixels of the planning data PDS.

With the use of the position data PI, a transfer of the segmentation to the thermometry data TDS or to the thermometry image data can take place in Step S5 using the thermometry data TDS and the segmentation data SDS that have been obtained in Step S3 and S2, respectively.

In a first presentation variant according to Step S6A, the segmentation data SDS are used as an edge or "border" to calculate a background phase for a "referenceless" generated PRFS image. One or more segmented structures that are described in the segmentation data are thereby selected, and a background phase is calculated based on the edge of the segmented structures. As noted, the calculation of the background phase to generate a "referenceless" PRFS image is known to the man skilled in the art and does not need to be repeated at this point. However, it is to be stressed that a calculation of a background phase that offers defined advantages for specific applications (for example a thermal ablation) is enabled via the selection of the "border" corresponding to the invention. The advantages are thereby achieved in that spatial transitions between different tissue types can be detected exactly in the planning data. As noted, the segmentation can nevertheless take place in a relatively course manner since the thermometry data TDS have a lower resolution than the planning data PDS. An automatic or computerized segmentation using the planning data is more robust than a manual determination of the region for the background phase using the thermometry data TDS. Overall, the calculation and creation of the PRFS images can thus be improved via a semi-automatic or fully automatic segmentation of the planning data.

In an embodiment of the method, the background phase determined on the basis of the segmentation can be used for one or more generated PRFS images. A reference information is thereby preferably recalculated for every PRFS image via segmentation of determined "borders". Moreover, an extension of the "referenceless method" is proposed which essentially represents a hybrid of "referenceless" and "reference-afflicted" calculation of the PRFS images. Given an unmodified region of the thermometric imaging, the repetition of the phase determination can thereby be repeated after an arbitrary number of images. For example, the background phase can be determined only for every second (every other) PFRS image (or for a number of intermediate images that is greater than two) based on respective newly measured MR thermometry data TDS. For example, the speed of the thermometry (and therefore likewise the use of the presentation by a user) can thus be improved overall since the generation of live images can be possible with an increased frame rate.

In a further variant of the method according to the invention according to Step S6B, image data are generated in which the position of the region of the examination subject that is detected via the thermometry image data is plotted in a three-dimensional representation. For example, this is clarified again later in connection with FIG. 5. For this purpose, the determined position data PI are used in order to generate a presentation which reflects the correct position of the region detected via the thermometry image data in the examination subject or, respectively, of a segmented structure. For example, the spatial orientation of an ablation instrument can thus be improved during an ablation and the monitoring of the ablation progress. Furthermore, interfering structures (for example large blood vessels) can be identified on the basis of the segmentation data SDS. Large blood vessels must not be injured during an ablation, but they increase the heat dissipation from the ablation area or the ROI. It is therefore particularly advantageous to make known their exact position during an ablation.

In a third variant for generation of the image data according to Step S6C, a fusion of the MR thermometry data TDS with the planning data PDS takes place. In particular, pixels of the planning data PDS are thereby superimposed with pixels of the thermometry data TDS. The fusion of planning data PDS with thermometry image data is similarly possible.

According to a fourth alternative to generate the image data that is described with regard to Step S6D, a limitation of the thermometry data TDS takes place to a "region of interest", in particular for an ablation. A region of the examination subject that is to be depicted thermometrically is thereby selected with the aid of segmentation data SDS, and the image data include thermometry image data only for the selected region. It is thus possible in particular to monitor the progress of an ablation method. For example, an exact percentile progress of an ablation method can be determined using the segmentation data SDS and be shown in the generated image data. For example, the segmentation data can be used in order to determine the percentile progress with regard to an ablation volume, since these segmentation data can include a region to be segmented that is identical to the region to be subject to an ablation. These can be areas or volumes that are used to calculate the percentile progress. The percentile ablation progress can be adopted into the generated image data as a presentation of a numerical value.

Each of the variants of the method can respectively be repeated, beginning with Step S3, in order to achieve a repeat generation of the image data (advantageously a current update with new temperature information). In particular, the generated image data are then "live image data". In principle, however, a repetition would also be conceivable using modified planning data according to Step S1.

Figure 3:
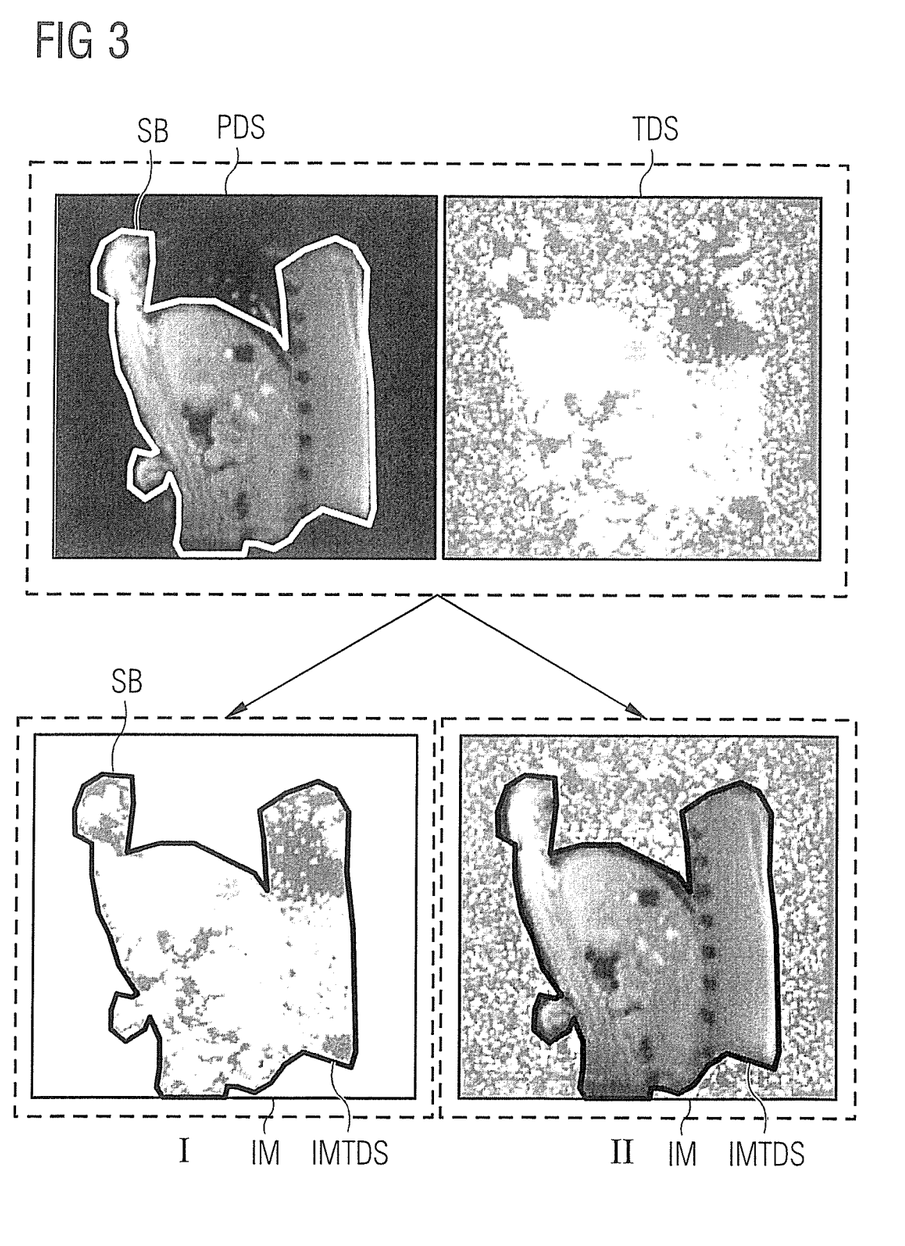
FIG. 3 illustrates the segmentation of thermometry image data using segmentation regions that are based on planning data, and the fusion of planning data with MR thermometry data.

FIG. 3 shows a few presentation variants of the image data in more detail. For example, a segmented structure SB can be selected by a user or automatically based on planning data PDS and/or—in the event that segmentation data SDS have been transferred to the thermometry data TDS—based on the thermometry data TDS. According to method Step S6D, in a presentation variant of the image data IM that is identified with I, only one image presentation IMTDS of the thermometry data TDS is generated in a region that is limited to the segmented structure SB. The focus of the observer is thus unambiguously diverted to its "region of interest", and it is possible to control the ablation specifically and precisely, for example. The progress of an ablation process in a defined plane is thus also intuitively recognizable. For example, this presentation variant can be further improved in that a fusion of the planning data PDS and the MR thermometry data TDS takes place according to Step S6C. This variant is labeled with II in FIG. 3. By superposition, the contrast (among other things that is provided via the thermometry data TDS is thereby improved via the contrast that is included in the planning data PDS. For example, in the concrete case color values (or equivalently greyscale values here) of individual pixels of the image data that are used to depict the thermometry data TDS can be added to color values that have been adopted from the planning data set PDS for the corresponding pixels, such that an additional contrasting takes place within the color presentation of the generated thermometry image data IMTDS, for example. The resolution of the planning data PDS is thereby preferably maintained. For example, the addition can also include a defined weighting, for example such that the contrast information from the planning data set receives less importance than the contrast information that is included in the MR thermometry data TDS.

Moreover, in the case of fusion the calculation of color values can also be based on the "Hue Saturation Lightness" color model. This color model is known to those skilled in the art and described by George H. Joblove and Donald Greenberg in "Color spaces for computer graphics", Computer Graphics (SIGGRAPH '78 Proceedings), 12(3):20-25, August 1978. A more detailed explanation is therefore not necessary herein.

It is particularly advantageous if the "lightness" (corresponding to the model) is taken from the planning data and provided for calculation of color values for the generated image data on the basis of the model. The "hue" data (i.e. the color-coded temperature information) are then taken from the thermometry image data and likewise used to generate the image data with the aid of the model.

Figure 4:
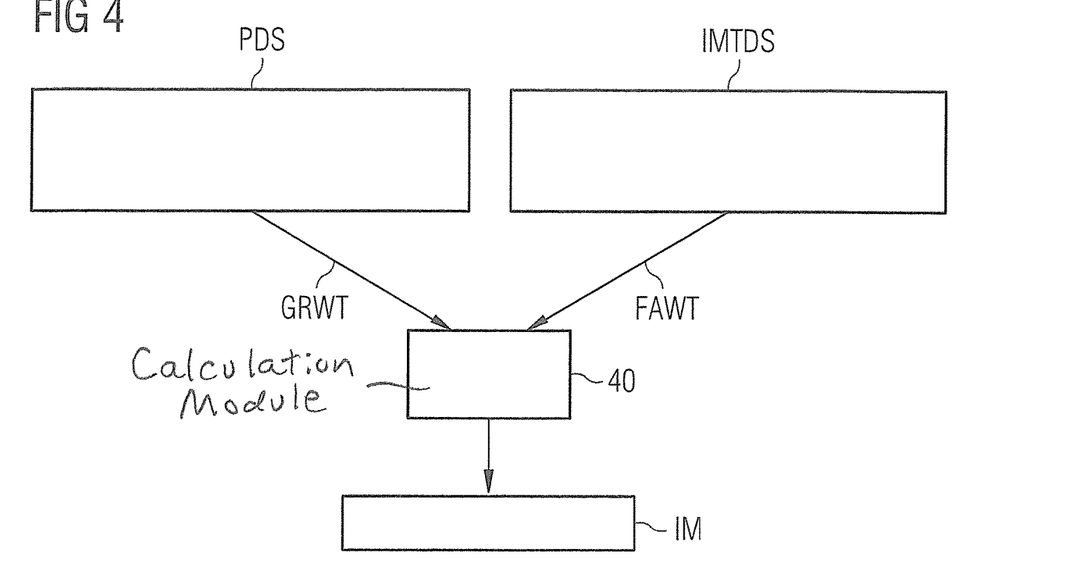
FIG. 4 is a schematic depiction of a method to determine color values of fused image data, wherein the fusion is based on the "Hue Saturation Lightness Model".

This is schematically shown in FIG. 4. Greyscale values of pixels or, respectively, voxels are adopted from the planning data PDS. This corresponds to the "lightness". The greyscale values that are adopted are preferably limited to "anatomical structures", which are represented by segmented structures, for example. A color-coded temperature value ("hue") is also adopted from the thermometry image data IMTDS. These two values, "hue" and "lightness", are communicated to the image data calculation module 40 (described in further detail with regard to FIG. 2). The image data calculation module 40 calculates fused image data IM on the basis of the "Hue Saturation Lightness" color model and the adopted "hue" and "lightness" values. The generated image data IM preferably have the spatial resolution of the aforementioned "high-resolution data" (i.e. either of the planning data or—in the event that the thermometry data are of higher resolution—the resolution of the thermometry data).

As an example, FIG. 4 shows anatomical information (limited to a segmented region, for example) as a planning data set PDS; color-coded temperature information as thermometry image data IMTDS; an HSL color model as an image data calculation module 40; fused image data as generated image data IM. The arrow GRWT also describes a greyscale value and the arrow FAWT describes a color value.

Figure 5:
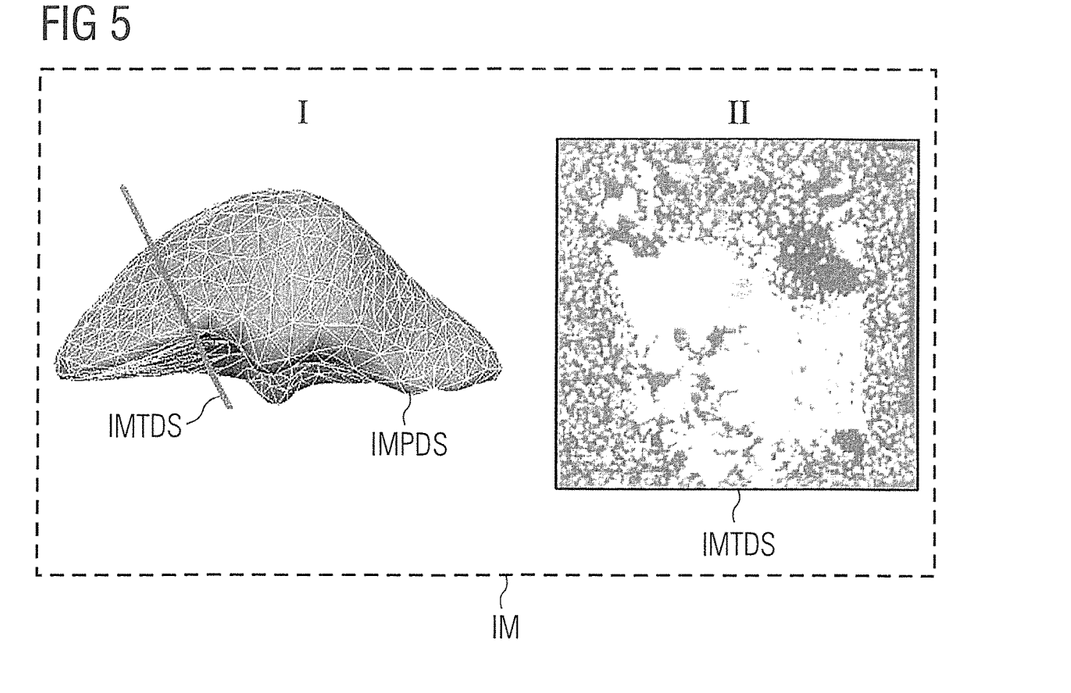
FIG. 5 shows the depiction of a segmented structure in the form of a 3D model in which the position of MR thermometry image data that are likewise shown is identified.

FIG. 5 shows an additional useful variant of the generation of image data IM that are obtained according to Steps S6B or S6A of the method corresponding to FIG. 1.

In a first segment of the image data IM that is identified with I, a 3D image IMPDS of a segmented structure of the planning data is shown. This is a 3D model of a liver which was adapted to the real relationships of the relative distances of defined points of the examination subject (for example defined landmarks) with the use of the segmentation data that were obtained from the planning data. In this 3D representation of a segmented structure, the position of a region that is described by the thermometry image data shown in a second segment II of the image data is indicated with the use of a line. The line represents the position of a slice plane with the liver, thus the organ which is represented by a presentation of the 3D model. In one presentation, for example, a slice plane could also be incorporated into the image data instead of the line. It is also possible for a superposition of the 3D image IMPDS with the thermometry image data IMTDS to take place in the region of the slice plane.

In the second segment (marked with II) of the image data IM, a PRFS thermometry image IMTDS that is calculated from the MR thermometry data according to Step S6A is shown. The background phase was determined based on segmentation data of the liver. Via image data IM that include these two presentations of the segments I and II, the user thus receives both a precise thermometry image IMTDS and a presentation of the position of the thermometry image IMTDS relative to the liver using the 3D image IMPDS of parts of the planning data.

Figure 2:
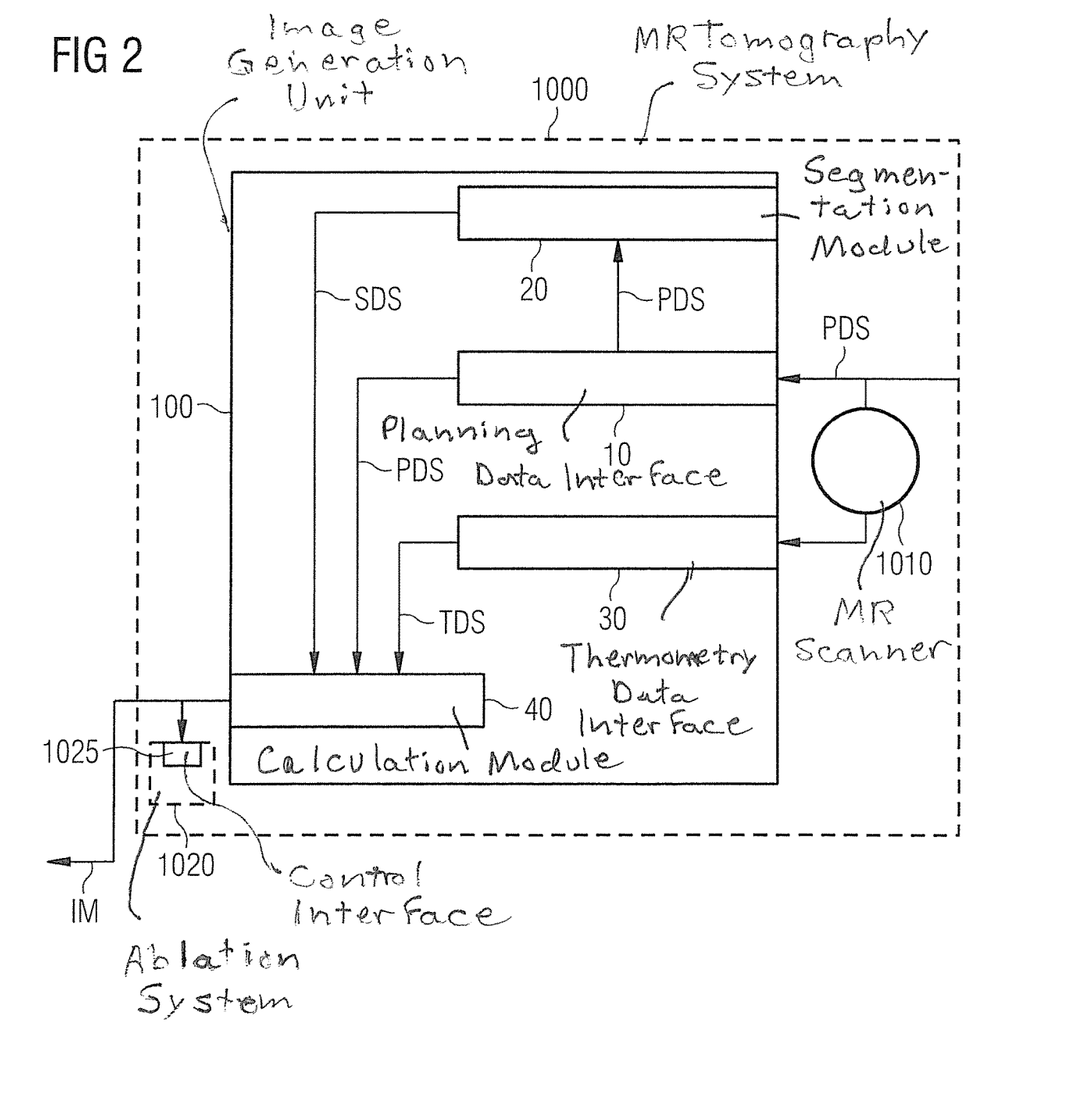
FIG. 2 shows an exemplary embodiment of a medical imaging system according to the invention, in a block diagram.

FIG. 2 shows an MR tomography system 1000 with an image data generation unit 100 and with an MR scanner 1010 that can acquire raw magnetic resonance data. Magnetic resonance image data can be calculated from the raw magnetic resonance data with the aid of a reconstruction unit (not shown) of the MR tomography system 1000. For example, if a thermal ablation is planned, high-resolution 3D data or a stack of 2D slice images of a patient that serve a planning data PDS for the ablation to be implemented are thus initially generated. These planning data PDS can be generated by different imaging systems; for example, computer tomography data or even ultrasound data are considered. However, the planning data PDS are particularly preferably generated with the use of the scanner 1010 of the MR tomography system 1000.

The planning data PDS are then used in order to plan the sequence of ablation steps, and possibly also in order to control an ablation system 1020 semi-automatically or fully automatically.

During the ablation, the MR tomography system 1000 used to generate the planning data PDS serves to generate MR thermometry data TDS which allow the determination of a temperature curve (temperature profile) within the examination subject. In particular, with the use of the shown MR tomography system 1000 it is possible to improve the presentation of the thermometry data TDS for use during the ablation.

For this, the tomography system 1000 has an image data generation unit 100 that is used to generate image data IM.

The image data generation unit 100 comprises a planning data interface 10 which can receive planning data PDS independent of the manner of their generation. The planning data interface 10 is preferably designed to receive data in DICOM format.

The image data generation unit 100 likewise has a thermometry data interface that is designed to receive thermometry data TDS. The thermometry data interface 30 is in particular connected with the scanner that provides thermometry data TDS in the form of magnitude images and phase images of an examination subject by means of a reconstruction unit of the tomography system 1000. Alternatively, magnitude and phase images can also be calculated from raw magnetic resonance data within the thermometry data interface, such that thermometry data TDS are also present in the form of magnitude images and phase images. The thermometry data interface 20 thus can itself be designed as a reconstruction unit or, respectively, can be a component of a reconstruction unit of the tomography system 1000.

The planning data PDS received by the planning data interface 10 are transmitted to both the segmentation module 20 and the image calculation module 40. The segmentation module 20 segments the planning data PDS and calculates one or more segmented structures. This information is assembled into segmentation data SDS and transferred from the segmentation module 20 to the image calculation module 40. The image calculation module 40 now calculates image data IM on the basis of the segmentation data SDS, the planning data PDS and the thermometry data TDS, according to one or more of the methods described with regard to FIG. 1.

With the use of the image data IM generated in such a manner, the operator of the ablation system 1020 can be supplied with valuable information in order to control a thermal ablation exactly and precisely.

To control the ablation, the image data (as control data, for example) can be transmitted to a control interface 1025 of the ablation system 1020, which control interface 1025 has been designed suitably for this. With the use of this interface 1025, the generated image data IM simultaneously enable a regulation of the ablation.

The invention thus provides a range of possibilities to improve the use of thermometry data or thermometry as a whole.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to generate and display image data based on magnetic resonance (MR) thermometry data, comprising:
    providing planning data to a computerized processor, said planning data having a spatial resolution and a contrast, and said planning data representing a region of an examination subject that it is to be depicted thermometrically;
    via said processor, segmenting a segmented region of the examination subject from said planning data;
    providing said processor with MR thermometry data having a resolution and a contrast that are lower than the spatial resolution and contrast of the planning data;
    via said processor, generating an MR thermometry image from said MR thermometry data;
    via said processor, bringing said MR thermometry image into registration with said planning data, thereby producing registered data;
    via said processor, using the registered data to transfer the segmented region of the examination subject from said planning data to said MR thermometry image, thereby obtaining a segmented MR thermometry image;
    via said processor, generating a 3D model of said segmented region of the examination subject from said planning data;
    via said processor, automatically generating 3D image data by superimposing said segmented MR thermometry image with said 3D model, with pixels of said 3D image data having grayscale values from said 3D model and hue values from said segmented MR thermometry image, so as to give a 3D image corresponding to said 3D image data the spatial resolution and contrast corresponding to said planning data and not the spatial resolution and contrast corresponding to said MR thermometry data; and
    at a display in communication with said processor, displaying said 3D image.

2. A method as claimed in claim 1 comprising acquiring the MR thermometry data that are provided to the processor with acquisition limitations dependent on structures that are contained in said segmented region of said examination subject from the planning data.

3. A method as claimed in claim 1 comprising, via said processor, determining background phase data from a segmented structure depicted in said segmented region of said examination subject from the planning data, and wherein generating said MR thermometry image comprises using said background phase data to generate said MR thermometry image as a proton resonance frequency shift thermometry image.

4. An image generation computer that generates and displays image data based on magnetic resonance (MR) thermometry data, comprising:
    a computerized processor;
    said processor having an input interface that receives planning data, said planning data having a spatial resolution and a contrast and said planning data representing a region of an examination subject that it is to be depicted thermometrically;
    said processor being configured to segment a segmented region of the examination subject from said planning data;
    said input interface also receiving MR thermometry data having a spatial resolution and a contrast that are lower than the spatial resolution and contrast of the planning data;
    said processor being configured to generate an MR thermometry image from said MR thermometry data;
    said processor being configured to bring said MR thermometry image into registration with said planning data, thereby producing registered data;
    said processor being configured to using the registered data to transfer the segmented region of the region of the examination subject from said planning to said MR thermometry image, thereby obtaining a segmented MR thermometry image;
    said processor being configured to generate a 3D model of said segmented region of the examination subject from said planning data;
    said processor being configured to generate 3D image data by superimposing said segmented MR thermometry image with said 3D model, with pixels of said 3D image data having grayscale values from said 3D model and hue values from said segmented MR thermometry image, so as to give a 3D image corresponding to said 3D image data the spatial resolution and contrast corresponding to said planning data and not the spatial resolution and contrast corresponding to said MR thermometry data; and
    a display in communication with said processor, at which said processor is configured to display said 3D image.

5. A medical imaging system that generates and displays image data based on magnetic resonance (MR) thermometry data, comprising:

an MR data acquisition scanner configured to acquire planning data having a spatial resolution and a contrast and representing a region of an examination subject that it is to be depicted thermometrically, and to acquire MR thermometry data having a spatial resolution and a contrast that are lower than the spatial resolution and contrast of the planning data from said region;

a computerized processor provided with said planning data and said MR thermometry data;

said processor being configured to segment a segmented region of the examination subject from said planning data;

via said processor being configured to generate an MR thermometry image from said MR thermometry data;

said processor being configured to bring said MR thermometry image into registration with said planning data, thereby producing registered data;

said processor being configured to using the registered data to transfer the segmented region of the examination subject from said planning data to said MR thermometry image, thereby obtaining a segmented MR thermometry image;

said processor being configured to generate a 3D model of said segmented region of the examination subject from said planning data;

said processor being configured to generate 3D image data by superimposing said segmented MR thermometry image with said 3D model, with pixels of said 3D image data having grayscale values from said 3D model and hue values from said segmented MR thermometry image, so as to give a 3D image corresponding to said 3D image data the spatial resolution and contrast corresponding to said planning data and not the spatial resolution and contrast corresponding to said MR thermometry data; and a display in communication with said processor, at which said processor is configured to display said 3D image.

6. A medical imaging system as claimed in claim 5 comprising an ablation system configured to implement an ablation procedure on the examination subject, said ablation system comprising an ablation system interface that receives said 3D image data from said processor, and said ablation system comprising an ablation system control unit configured to operate the ablation system to execute said ablation procedure dependent on said 3D image data.

7. A non-transitory, computer-readable data storage medium encoded with programming instructions, said programming instructions configured to cause a processor to:

receive planning data having a spatial resolution and a contrast and representing a region of an examination subject that it is to be depicted thermometrically;

segment a segmented region of the examination subject from said planning data;

receive magnetic resonance (MR) thermometry data, having a spatial resolution and a contrast that are lower than the spatial resolution and contrast of the planning data;

generate an MR thermometry image from said MR thermometry data;

bring said MR thermometry image into registration with said planning data, thereby producing registered data;

use the registered data to transfer the segmented region of the examination subject from said planning data to said MR thermometry image, thereby obtaining a segmented MR thermometry image;

generate a 3D model of said segmented region of the examination subject from said planning data;

generate 3D image data by superimposing said segmented MR thermometry image with said 3D model, with pixels of said 3D image data having grayscale values from said 3D model and hue values from said segmented MR thermometry image, so as to give a 3D image corresponding to said 3D image data the spatial resolution and contrast corresponding to said planning data and not the spatial resolution and contrast corresponding to said MR thermometry data; and at a display in communication with said processor, display said 3D image.

* * * * *